US012629000B2

(12) United States Patent
Imoto et al.

(10) Patent No.: US 12,629,000 B2
(45) Date of Patent: May 19, 2026

(54) EXAMINATION SUPPORT DEVICE, EXAMINATION SUPPORT METHOD, AND EXAMINATION SUPPORT PROGRAM FOR SEQUENTIALLY ACQUIRING IMAGE SIGNAL CORRESPONDING TO DISPLAY IMAGE

(71) Applicant: AI Medical Service Inc., Tokyo (JP)

(72) Inventors: Yuya Imoto, Tokyo (JP); Shinichi Fuchita, Tokyo (JP)

(73) Assignee: AI Medical Service Inc., Tokyo (JP)

( * ) Notice: Subject to any disclaimer, the term of this patent is extended or adjusted under 35 U.S.C. 154(b) by 442 days.

(21) Appl. No.: 18/125,497

(22) Filed: Mar. 23, 2023

(65) Prior Publication Data
US 2023/0263366 A1 Aug. 24, 2023

Related U.S. Application Data

(63) Continuation of application No. PCT/JP2021/034081, filed on Sep. 16, 2021.

(30) Foreign Application Priority Data
Sep. 23, 2020 (JP) ................................. 2020-158885

(51) Int. Cl.
*A61B 1/00* (2006.01)
*A61B 1/05* (2006.01)

(52) U.S. Cl.
CPC .. *A61B 1/000094* (2022.02); *A61B 1/000096* (2022.02); *A61B 1/0005* (2013.01); *A61B 1/05* (2013.01)

(58) Field of Classification Search
CPC ........ A61B 1/000094; A61B 1/000096; A61B 1/0005; A61B 1/05; A61B 1/00009;
(Continued)

(56) References Cited

U.S. PATENT DOCUMENTS

2002/0138008 A1 9/2002 Tsujita et al.
2003/0189654 A1 10/2003 Kage et al.
(Continued)

FOREIGN PATENT DOCUMENTS

JP 2003-099783 A 4/2003
JP 2003-296713 A 10/2003
(Continued)

OTHER PUBLICATIONS

Iwaoka Naoki et al., Trade-off Analysis for Polyp Segmentation of NBI Images 17th SSII2011 Yokohama Jun. 30, 2011, pp. ISI-09-1-ISI-09-7.

*Primary Examiner* — Kent Yip
(74) *Attorney, Agent, or Firm* — PROCOPIO, CORY, HARGREAVES & SAVITCH LLP

(57) ABSTRACT

There is provided an examination support device that is used by being connected to an endoscope system including a camera unit for being inserted into an inside of a body of a subject, the examination support device including an acquisition unit for sequentially acquiring an image signal that the endoscope system provides to an external device; a detection unit for detecting a difference between successive frame images in relation to frame images that are sequentially generated from the image signals; and an establishing unit for establishing an image region indicating a captured image that is captured by the camera unit, based on a region of change where an amount of difference of the difference detected by the detection unit is equal to or greater than a reference amount.

7 Claims, 10 Drawing Sheets

(58) Field of Classification Search
CPC .......... A61B 1/045; G06T 2207/10068; G06T 2207/20081; G06T 2207/20084; G06T 2207/20132; G06T 2207/30092; G06T 2207/30096; G06T 7/0012; G06T 7/11
See application file for complete search history.

(56) References Cited

U.S. PATENT DOCUMENTS

| 2015/0097976 A1 | 4/2015 | Nakanishi et al. |
| 2018/0253839 A1* | 9/2018 | Zur ................. A61B 1/000094 |
| 2019/0073768 A1* | 3/2019 | Shigeta ........... A61B 1/000094 |
| 2021/0186315 A1* | 6/2021 | Oosake ............... A61B 1/0638 |
| 2021/0196100 A1 | 7/2021 | Godo et al. |
| 2022/0414873 A1* | 12/2022 | Kimura ................. G16H 30/20 |

FOREIGN PATENT DOCUMENTS

| JP | 2006-246110 A | 9/2006 | |
| JP | 2019-042156 A | 3/2019 | |
| WO | 2013/080245 A1 | 6/2013 | |
| WO | 2013/088688 A1 | 6/2013 | |
| WO | 2019/216084 A | 11/2019 | |
| WO | 2020/059098 A1 | 3/2020 | |
| WO | 2020/071678 A2 | 4/2020 | |
| WO | WO2020071678 * | 4/2020 | ............. G16H 50/20 |

* cited by examiner

225

221

REGENERATED IMAGE REGENERATED
FROM DISPLAY SIGNAL

222

CUTTING OUT OF IMAGE REGION

121

REPRODUCED
CAPTURED IMAGE

151

REDUCED DISPLAY
ON DISPLAY MONITOR 122b    122   120

ESTIMATED
PROBABILITY

121

DISPLAY DIAGNOSIS
SUPPORT INFORMATION

85%

122c     122a

DIFFERENCE IMAGE $d_n$

DIFFERENCE IMAGE $d_{n+1}$

ESTABLISH CANDIDATE IMAGE REGION (a)                                          (b)

121

151

ESTIMATED PROBABILITY:p%

1

EXAMINATION SUPPORT DEVICE, EXAMINATION SUPPORT METHOD, AND EXAMINATION SUPPORT PROGRAM FOR SEQUENTIALLY ACQUIRING IMAGE SIGNAL CORRESPONDING TO DISPLAY IMAGE

CROSS REFERENCE TO RELATED APPLICATION

The present application is based upon and claims the benefit of priority from Japanese Patent Application No. 2020-158885, filed on Sep. 23, 2020, and International application No. PCT/JP2021/034081 filed on Sep. 16, 2021, the entire contents of which are hereby incorporated by reference.

TECHNICAL FIELD

The present invention relates to an examination support device, an examination support method, and an examination support program.

BACKGROUND ART

There is known an endoscope system that captures an inside of a stomach, for example, of a subject by an endoscope and that displays an image of it on a monitor. These days, examination support devices that analyze an image captured by an endoscope system and that notify a doctor of a result of it are becoming widespread (for example, see Patent Literature 1).

CITATION LIST

Patent Literature

Patent Literature 1: Japanese Patent Laid-Open No. 2019-42156

SUMMARY OF INVENTION

Technical Problem

A system where an examination support device takes in and analyzes, in an ex-post manner, an in-body image of a subject captured by an endoscope system lacks instantaneity. A doctor examining a subject wants to instantaneously grasp an analysis result in conjunction with capturing of an inside of a body by the endoscope system. Accordingly, a mode of use is conceivable according to which the examination support device is connected to the endoscope system and the in-body image captured by the endoscope system is analyzed by the examination support device in approximately real time. In this case, the examination support device is able to receive an image signal that the endoscope system provides to an external device. However, such an image signal is a display signal used, for example, by the endoscope system to display a processing result and the like on a system monitor of the endoscope system, and often also includes a display signal related to examination information and the like in addition to the image signal of the in-body image. Accordingly, to enable the examination support device to analyze the in-body image, an image region corresponding to the in-body image has to be appropriately cut out from an image region corresponding to the image signal that is provided by the endoscope system.

2

The present invention has been made to solve a problem as described above, and is aimed at providing an examination support device and the like for appropriately cutting out an image region indicating a captured image that is captured by an endoscope system, from an image signal that is transmitted from the endoscope system, and for providing the image region to be used in image analysis.

Solution to Problem

An examination support device according to a first mode of the present invention is an examination support device that is used by being connected to an endoscope system including a camera unit for being inserted into an inside of a body of a subject, the examination support device including: an acquisition unit for sequentially acquiring an image signal that the endoscope system provides to an external device; a detection unit for detecting a difference between successive frame images in relation to frame images that are sequentially generated from the image signals; and an establishing unit for establishing an image region indicating a captured image that is captured by the camera unit, based on a region of change where an amount of difference of the difference detected by the detection unit is equal to or greater than a reference amount.

An examination support method according to a second mode of the present invention is an examination support method performed using an examination support device that is used by being connected to an endoscope system including a camera unit for being inserted into an inside of a body of a subject, the examination support method including: an acquisition step of sequentially acquiring an image signal that the endoscope system provides to an external device; a detection step of detecting a difference between successive frame images in relation to frame images that are sequentially generated from the image signals; and an establishing step of establishing an image region indicating a captured image that is captured by the camera unit, based on a region of change where an amount of difference of the difference detected in the detection step is equal to or greater than a reference amount.

An examination support program according to a third mode of the present invention is an examination support program for controlling an examination support device that is used by being connected to an endoscope system including a camera unit for being inserted into an inside of a body of a subject, the examination support program being for causing a computer to perform: an acquisition step of sequentially acquiring an image signal that the endoscope system provides to an external device; a detection step of detecting a difference between successive frame images in relation to frame images that are sequentially generated from the image signals; and an establishing step of establishing an image region indicating a captured image that is captured by the camera unit, based on a region of change where an amount of difference of the difference detected in the detection step is equal to or greater than a reference amount.

Advantageous Effects of Invention

According to the present invention, there may be provided an examination support device and the like for appropriately cutting out an image region indicating a captured image that is captured by an endoscope system, from an image signal that is transmitted from the endoscope system, and for providing the image region to be used in image analysis.

DESCRIPTION OF EMBODIMENT

Hereinafter, the present invention will be described based on an embodiment of the invention, but the invention according to the claims is not limited to the embodiment described below. Moreover, not all the configurations described in the embodiment are essential as means for solving the problems.

Figure 1:
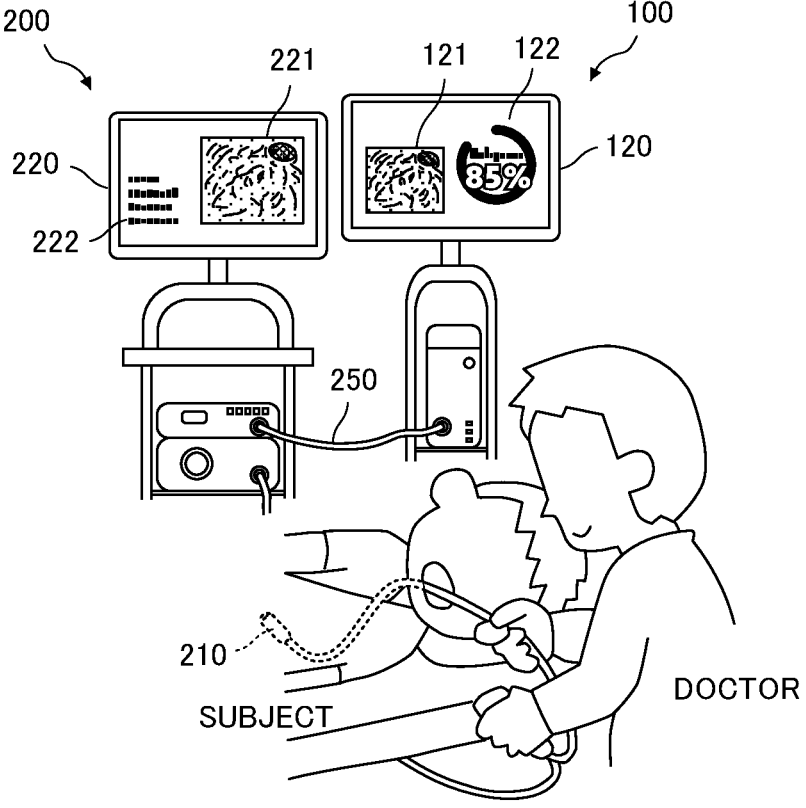
FIG. 1 is a diagram showing a manner of an endoscopic examination performed using an endoscope system and an examination support device according to a present embodiment.

FIG. 1 is a diagram showing a manner of an endoscopic examination performed using an endoscope system 200 and an examination support device 100 according to a present embodiment. The endoscope system 200 and the examination support device 100 are both installed in a consultation space. The present embodiment assumes a case where, of an inside of a body of a subject, a stomach is examined. The endoscope system 200 includes a camera unit 210, and as shown in the drawing, the camera unit 210 is inserted into the stomach of a subject who is lying down, through a mouth, and transmits, to a system main body, an image signal of an image that is obtained by capturing an inside of the stomach. Insertion of the camera unit 210 into the stomach and an image capturing operation are performed by a doctor.

The endoscope system 200 includes a system monitor 220 that is configured by a liquid crystal panel, for example, and processes the image signal transmitted from the camera unit 210 and displays the same as a captured image 221 that can be viewed, on the system monitor 220. Furthermore, the endoscope system 200 displays examination information 222 including subject information, camera information about the camera unit 210, and the like on the system monitor 220.

The examination support device 100 is connected to the endoscope system 200 by a connection cable 250. The endoscope system 200 transmits a display signal that is transmitted to the system monitor 220, also to the examination support device 100 via the connection cable 250. That is, the display signal in the present embodiment is an example of an image signal that is provided to an external device by the endoscope system 200. The examination support device 100 includes a display monitor 120 that is configured by a liquid crystal panel, for example, and extracts an image signal corresponding to the captured image 221 from the display signal that is transmitted from the endoscope system 200, and displays the same as a captured image 121 that can be viewed, on the display monitor 120. Furthermore, the examination support device 100 generates and analyzes image data of the captured image 121, outputs diagnosis support information 122, and displays the same on the display monitor 120. The examination support device 100 displays the captured image 121 or the diagnosis support information 122 as soon as the display signal is received from the endoscope system 200 or in synchronization with a timing when an operation of the camera unit 210 by the doctor is estimated. That is, the doctor is able to sequentially check the captured image 121 and the diagnosis support information 122 synchronously with progress of examination.

In the case where the examination support device 100 is used by being connected to an existing endoscope system 200, a dedicated signal convenient for the examination support device 100 is not received, but a general-purpose image signal that the endoscope system 200 provides to an external device, such as the display signal, is used. The general-purpose image signal includes an image signal corresponding to the captured image that is captured by the camera unit 210, but also includes image signals corresponding to information associated with examination and a GUI. To enable the examination support device 100 to analyze the captured image that is captured by the camera unit 210, an image region corresponding to the captured image has to be appropriately cut out from an image region corresponding to the image signal received from the endoscope system 200 and image data of the captured image has to be regenerated. Accordingly, the examination support device 100 according to the present embodiment appropriately establishes an image region of the captured image captured by the camera unit 210 in the image region corresponding to the image signal received from the endoscope system 200. Once the image region is established, the examination support device 100 may swiftly and stably sequentially generate image data for image analysis from image signals that are subsequently received. In the following, a configuration of the examination support device 100, processing procedures, modifications and the like will be successively described.

Figure 2:
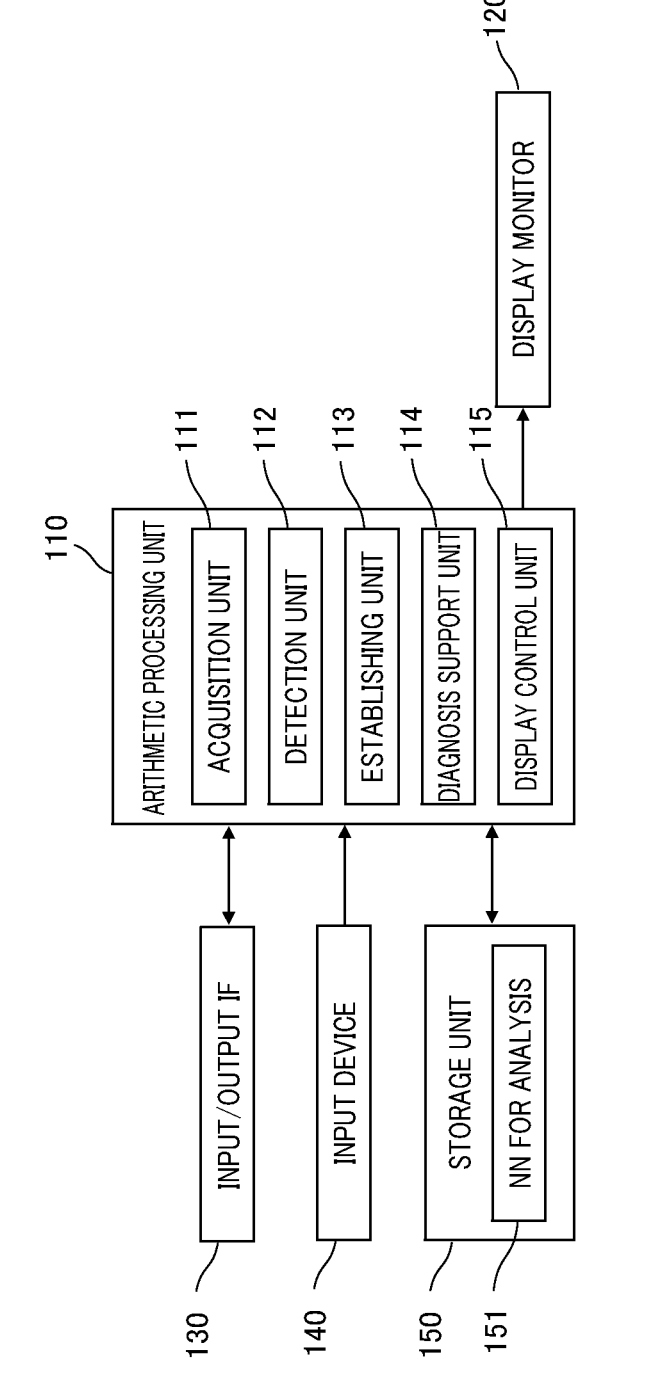
FIG. 2 is a hardware configuration diagram of the examination support device.

FIG. 2 is a hardware configuration diagram of the examination support device 100. The examination support device 100 mainly includes an arithmetic processing unit 110, a display monitor 120, an input/output interface 130, an input device 140, and a storage unit 150. The arithmetic processing unit 110 is a processor (CPU: Central Processing Unit) that performs processes of controlling the examination support device 100 and executing programs. The processor may operate in conjunction with an arithmetic processing chip such as an application specific integrated circuit (ASIC) or a graphics processing unit (GPU). The arithmetic processing unit 110 performs various processes related to supporting of examination by reading out an examination support program that is stored in the storage unit 150.

As described above, the display monitor 120 is a monitor including a liquid crystal panel, for example, and the display monitor 120 displays the captured image 121, the diagnosis support information 122 in a visible manner. The input/output interface 130 is a connection interface that includes a connector for connecting the connection cable 250, and that is for exchanging information with an external appliance. The input/output interface 130 includes a LAN unit, for example, and takes in the examination support program and update data for a neural network for analysis 151 described later from an external appliance and transfers the same to the arithmetic processing unit 110.

The input device 140 is a keyboard, a mouse, or a touch panel that is superimposed on the display monitor 120, for example, and a doctor or an assistant operates the same to change settings of the examination support device 100 and to input information necessary for examination.

The storage unit 150 is a non-volatile storage medium, and is configured by a hard disk drive (HDD), for example. The storage unit 150 is capable of storing, in addition to programs for controlling the examination support device 100 and for executing processes, various parameter values to be used for control and calculation, functions, display element data, look-up tables, and the like. In particular, the storage unit 150 stores the neural network for analysis 151. The neural network for analysis 151 is a trained model for calculating, when image data captured by the camera unit 210 is input, a probability of existence of a lesion in a corresponding image. Additionally, the storage unit 150 may be configured by a plurality of pieces of hardware, and for example, a storage medium for storing programs, and a storage medium for storing the neural network for analysis 151 may be configured by separate pieces of hardware.

The arithmetic processing unit 110 also serves a role of an arithmetic functional unit that performs various calculations according to processes which the examination support program instructs the arithmetic processing unit 110 to perform. The arithmetic processing unit 110 may function as an acquisition unit 111, a detection unit 112, an establishing unit 113, a diagnosis support unit 114, and a display control unit 115. The acquisition unit 111 sequentially acquires display signals that are transmitted from the endoscope system 200, develops each into a frame image, and transfers the frame image to the detection unit 112. The detection unit 112 receives the frame images that are sequentially generated by the acquisition unit 111, and detects a difference between successive frame images. The establishing unit 113 establishes an image region indicating a captured image that is captured by the camera unit 210, by retrieving a region of change in a difference image that is expressed by an amount of difference of the difference detected by the detection unit 112, the region of change being where the amount of difference is equal to or greater than a reference amount. The diagnosis support unit 114 inputs the captured image 121 that is generated during examination of the stomach to the neural network for analysis 151 read from the storage unit 150, causes the probability of existence of a lesion to be calculated, and generates the diagnosis support information. The display control unit 115 controls display on the display monitor 120 by generating a display signal of a display page that is to be displayed on the display monitor 120 and transmitting the display signal to the display monitor 120.

Figure 3:
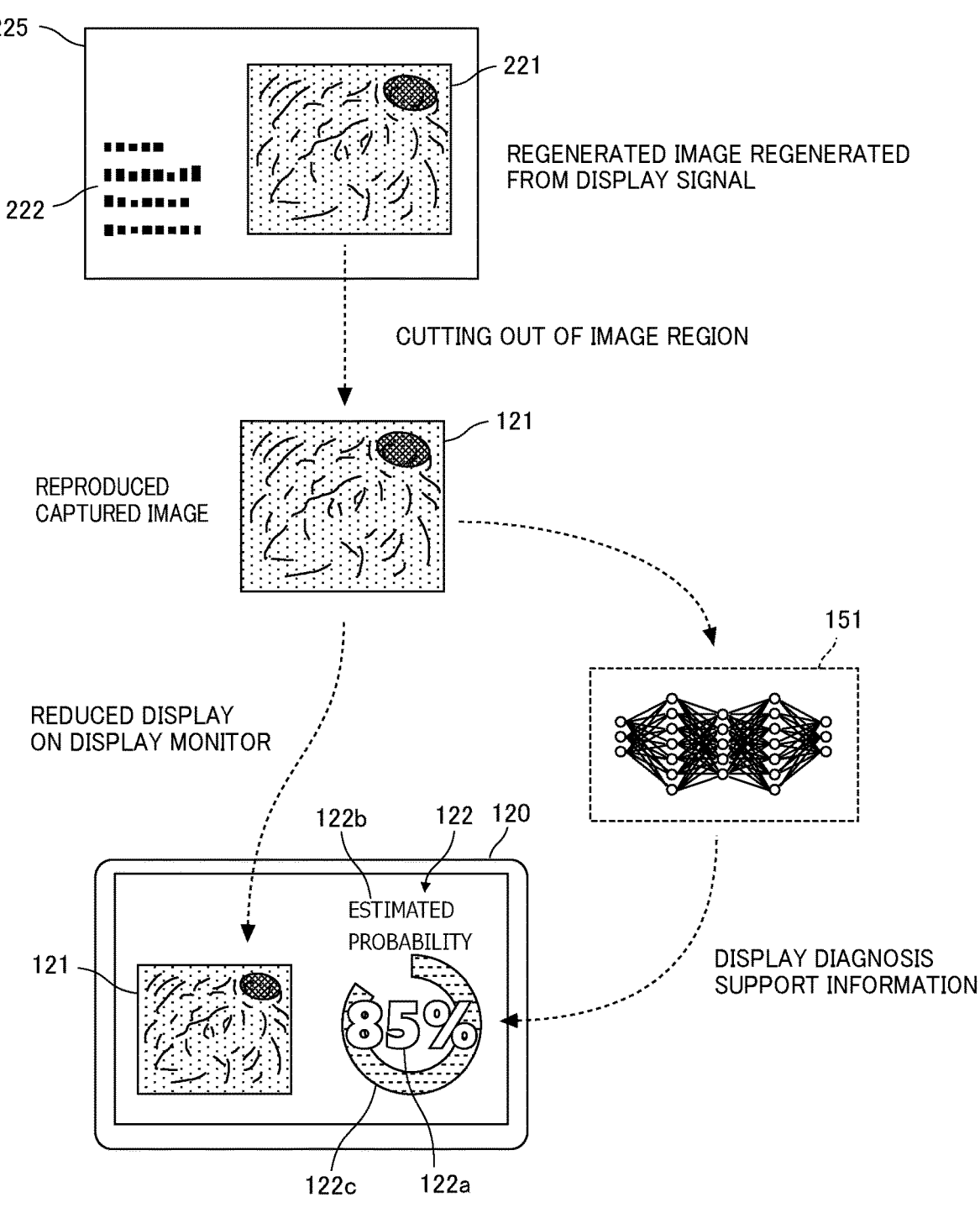
FIG. 3 is a diagram describing a process up to generation of a display page from a display signal that is received at a time of examination.

FIG. 3 is a diagram describing a process up to generation of a display page on the display monitor 120 from a display signal that is received at the time of examination. A regenerated signal image 225 that is a frame image that is obtained by the acquisition unit 111 acquiring and developing a display signal transmitted from the endoscope system 200 is the same as a display image that is displayed on the system monitor 220 of the endoscope system 200. As described above, the regenerated signal image 225 includes the captured image 221 and the examination information 222. The examination information 222 here is assumed to be text information, but may also include information other than the text information, such as computer graphics.

In a case where which region in an image region of the regenerated signal image 225 is the image region indicating the captured image is established before examination is started, as described below, the acquisition unit 111 cuts out the established image region as the captured image 121. The captured image 121 can practically be said to be an image that is obtained by reproducing the captured image captured by the camera unit 210 by the examination support device 100. The acquisition unit 111 transfers captured image data of the captured image 121 that is reproduced in the above manner to the diagnosis support unit 114 and the display control unit 115.

The diagnosis support unit 114 inputs to the neural network for analysis 151, the captured image data that is received, causes an estimated probability of existence of a lesion in the image to be calculated, and transfers a result of it to the display control unit 115. The display control unit 115 displays the captured image data received from the acquisition unit 111 and the diagnosis support information including the estimated probability received from the diagnosis support unit 114 on the display monitor 120 by developing and arranging the same according to a display mode set in advance. More specifically, as shown in a bottom drawing in FIG. 3, for example, the captured image 121 is reduced and arranged on a left side, and the diagnosis support information 122 is arranged on a right side while being segmented into elements including numerical value information 122a indicating the estimated probability, title text 122b, and circle graph graphics 122c. Additionally, such a display mode is merely an example, and each display element is not necessarily displayed during examination.

Figure 4:
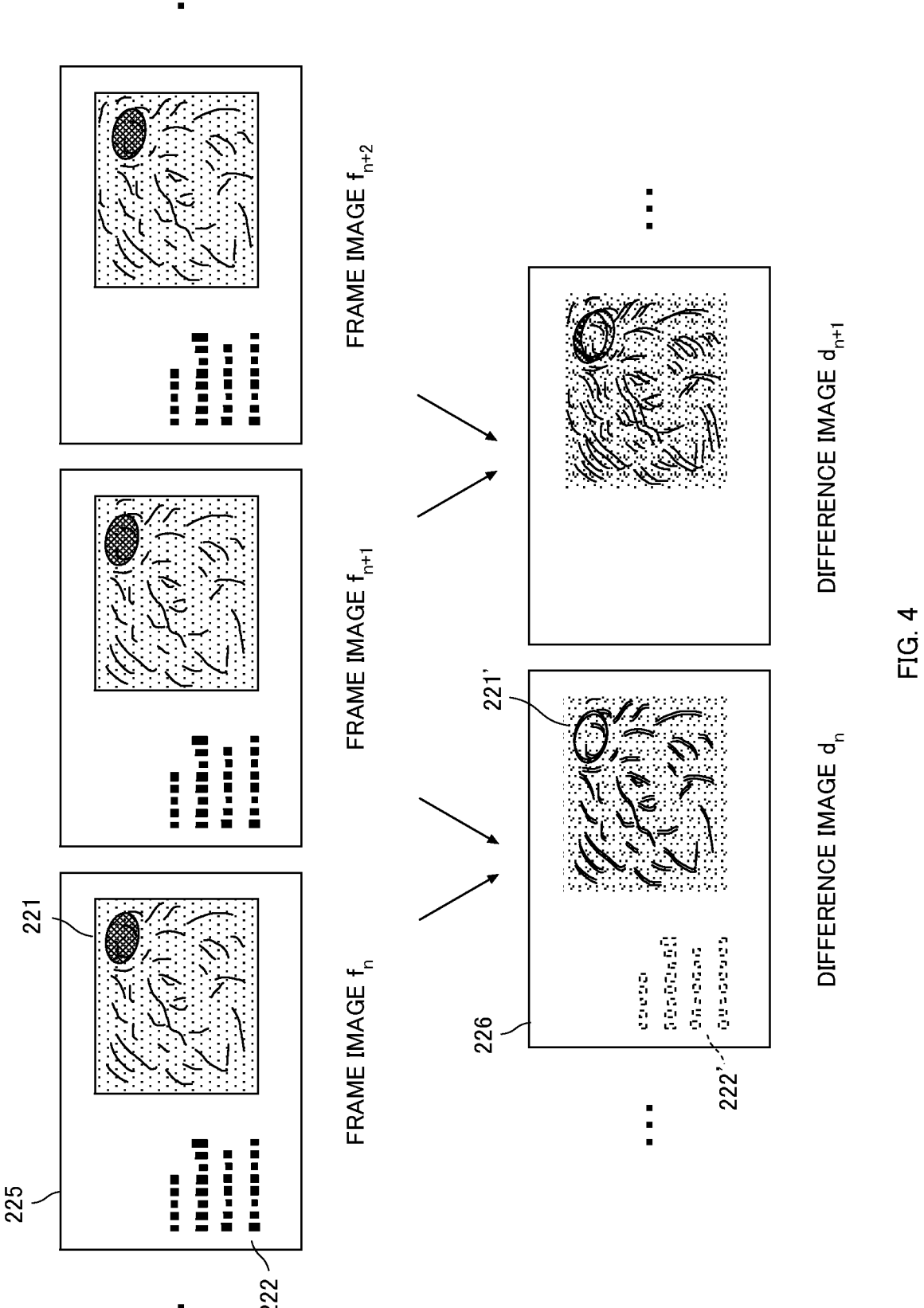
FIG. 4 is a diagram describing a process by a detection unit.

Next a process up to establishment of an image region indicating the captured image in the image region of the regenerated signal image 225 will be described. FIG. 4 is a diagram describing a process by the detection unit 112. Capturing by the camera unit 210 of the endoscope system 200 is performed at 60 fps, for example. The endoscope system 200 sequentially generates the display signal in response. Accordingly, the acquisition unit 111 generates frame images at 60 fps, for example, from display signals that are sequentially acquired.

In a top section in FIG. 4, the frame images that are sequentially received by the detection unit 112 from the acquisition unit 111 are chronologically arranged from left to right. More specifically, a frame image $f_n$, a frame image $f_{n+1}$, and a frame image $f_{n+2}$ that are three frame images that are successively received at a certain time point are schematically shown.

The detection unit 112 detects a difference between two successive frame images (in this case, a pair of the frame image $f_n$ and the frame image $f_{n+1}$, and a pair of the frame image $f_{n+1}$ and the frame image $f_{n+2}$). More specifically, each frame image is converted into gray scale, a difference in pixel values is calculated between corresponding pixels as an amount of difference, and a difference image 226 is thus generated. A bottom section in FIG. 4 shows the thus generated difference images 226 next to each other. More specifically, a difference image $d_n$ that is generated from the frame image $f_n$ and the frame image $f_{n+1}$, and a difference image $d_{n+1}$ that is generated from the frame image $f_{n+1}$ and the frame image $f_{n+2}$ are schematically shown. Additionally, in this case, the difference image is generated from frame images that are adjacent to each other among successive frame images, but the difference image does not have to be generated from successive frame images, and the difference image may instead be generated by extracting the frame image from successive frame images every ten frames, for example.

As described above, the regenerated signal image 225 that is sequentially generated as the frame image includes the captured image 221 and the examination information 222. Of these, the captured image 221 is updated according to an output rate of the camera unit 210, and is thus changed over time on a per-frame basis unless the camera unit 210 is capturing a non-moving target while being in a fixed state. Accordingly, in the difference image 226, corresponding pixels belonging to a region corresponding to the captured image 221 each indicate relatively great amounts of difference, and a region including the corresponding pixels is made apparent as a region of change 221'.

Meanwhile, the examination information 222 does not change over time on a per-frame basis, and even in a case where text that is displayed is to be rewritten, for example, frequency of it is substantially lower than a frame rate. Accordingly, in most cases, in the difference image 226, corresponding pixels belonging to a region corresponding to the examination information 222 each indicate zero or a small amount of difference, and the region including the corresponding pixels may be evaluated to be a region of no change 222'. The detection unit 112 transfers the difference image 226 that is expressed by the amount of difference between the frame images, to the establishing unit 113. The establishing unit 113 determines the region of change 221' from the difference image 226 that is received, and establishes the image region indicating the captured image based on the region of change 221'.

Figure 5:
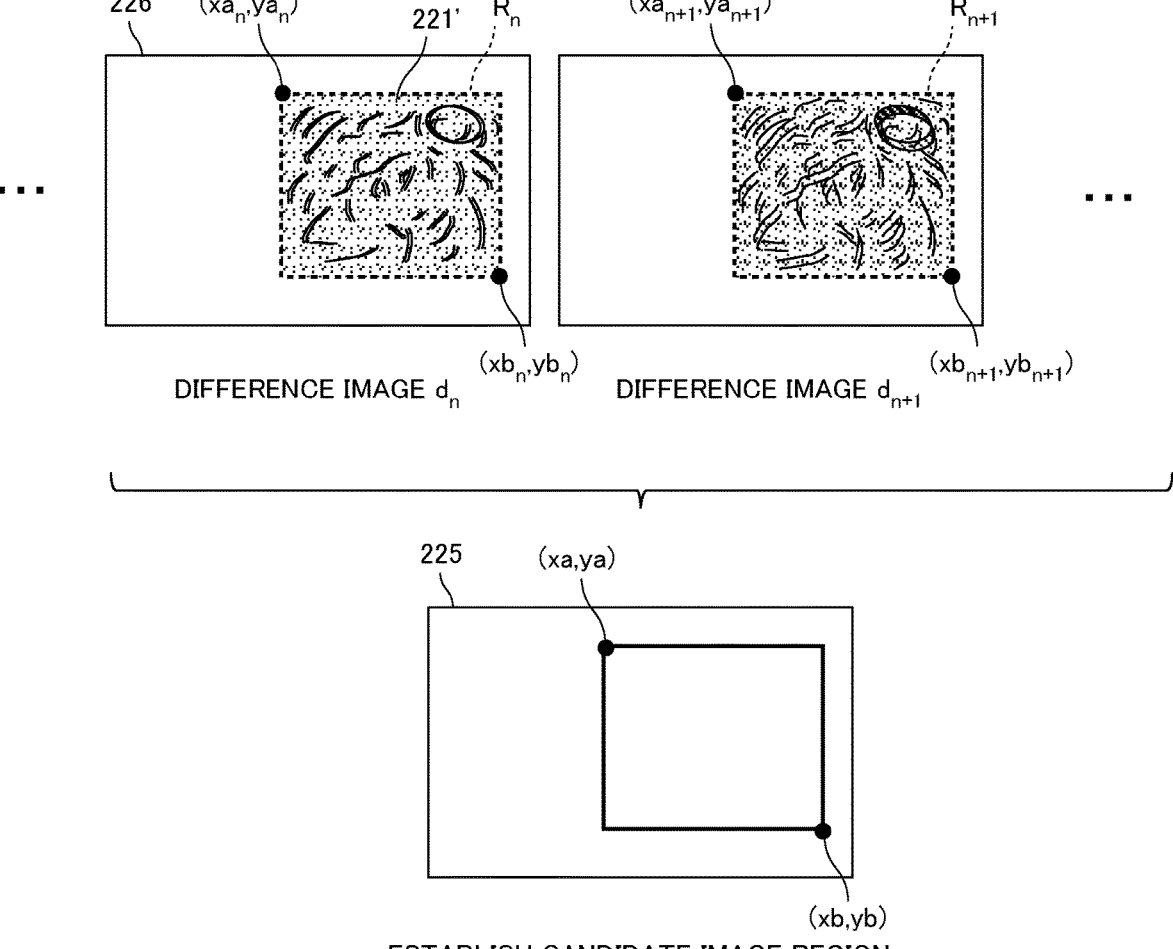
FIG. 5 is a diagram describing a process by an establishing unit.

FIG. 5 is a diagram describing a process by the establishing unit 113. In a top section in FIG. 5, as in the bottom section in FIG. 4, the difference images 226 that are generated are arranged in order of generation. The establishing unit 113 first determines the region of change 221' from the difference image 226 that is received. More specifically, sorting is performed based on whether the amount of difference at each pixel forming the difference image 226 is equal to or greater than the reference amount, and a block of region including the pixels with respect to which the amount of difference is determined to be equal to or greater than the reference amount is taken as the region of change 221'. The reference amount here is set to a value that is adjusted in advance through trial and error such that a region corresponding to the captured image 221 may be appropriately extracted. Furthermore, pixels where the amount of difference is smaller than the reference amount may be discretely included in the region of change 221'. For example, when 80 or more pixels where the amount of difference is equal to or greater than the reference amount are present in a range of 10 pixels×10 pixels, such a range is wholly included in the region of change 221'.

When the region of change 221' is determined in the above manner, the establishing unit 113 then determines a rectangular region R that is included inside the region of change 221' with respect to each difference image 226. As shown in the drawing, with respect to a rectangular region $R_n$ determined in relation to the difference image $d_n$, top left coordinates are $(xa_n, ya_n)$, and bottom right coordinates are $(xb_n, yb_n)$. Similarly, with respect to a rectangular region $R_{n+1}$ determined in relation to the difference image $d_{n+1}$, top left coordinates are $(xa_{n+1}, ya_{n+1})$, and bottom right coordinates are $(xb_{n+1}, yb_{n+1})$.

The establishing unit 113 calculates average coordinates (xa, ya) of the top left coordinates and average coordinates (xb, yb) of the bottom right coordinates with respect to the rectangular region R that is determined in relation to each of a specified number of difference images (for example, eight difference images) that are successively generated, and establishes a candidate image region in relation to the image region of the regenerated signal image 225. Additionally, the establishing unit 113 may further adjust the candidate image region that is calculated in the above manner to an aspect ratio or a size that is set in advance. For example, in a case where the aspect ratio of an image that can be input to the neural network for analysis 151 is set, a rectangular shape of the candidate image region may be adjusted to match the aspect ratio.

Figure 6:
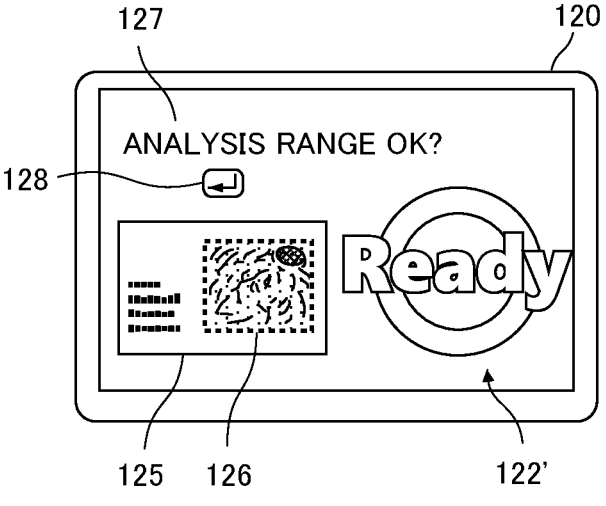
FIG. 6 is a diagram showing an example of an agreement page for receiving agreement of a doctor.

The establishing unit 113 may establish the candidate image region that is calculated in the above manner to be the image region indicating the captured image captured by the camera unit 210 as it is, but here, the candidate image region is established as the image region after being checked and agreed to by a doctor who is a user. FIG. 6 is a diagram showing an example of an agreement page for receiving agreement of the doctor.

The agreement page includes a regenerated signal image 125 that is the regenerated signal image 225 that is displayed in a reduced manner, inquiry text 127 that is text information requesting agreement to an analysis range, an enter icon 128 indicating an operation button, and support information 122' indicating a preparation stage before examination. A region outline indicator 126 is displayed superimposed on the regenerated signal image 125 so that the candidate image region that is established can be visually recognized.

The doctor checks whether the region outline indicator 126 correctly surrounds the image region indicating the captured image, and taps the enter icon 128 when there is no problem. When the tap is recognized through a touch panel that is one of the input devices 140, the establishing unit 113 establishes the candidate image region as the image region indicating the captured image that is captured by the camera unit 210.

The examination support device 100 establishes which region in the image region of the regenerated signal image 225 that is generated from the image signal that is sequentially received is the image region indicating the captured image, before examination of the inside of the stomach is started. Accordingly, at a stage of examination of the inside of the stomach, the image data of the captured image 121 may be generated by cutting out an established fixed region from the image region of the regenerated signal image 225, which helps analysis by the diagnosis support unit 114 be swiftly and stably performed.

Figure 7:
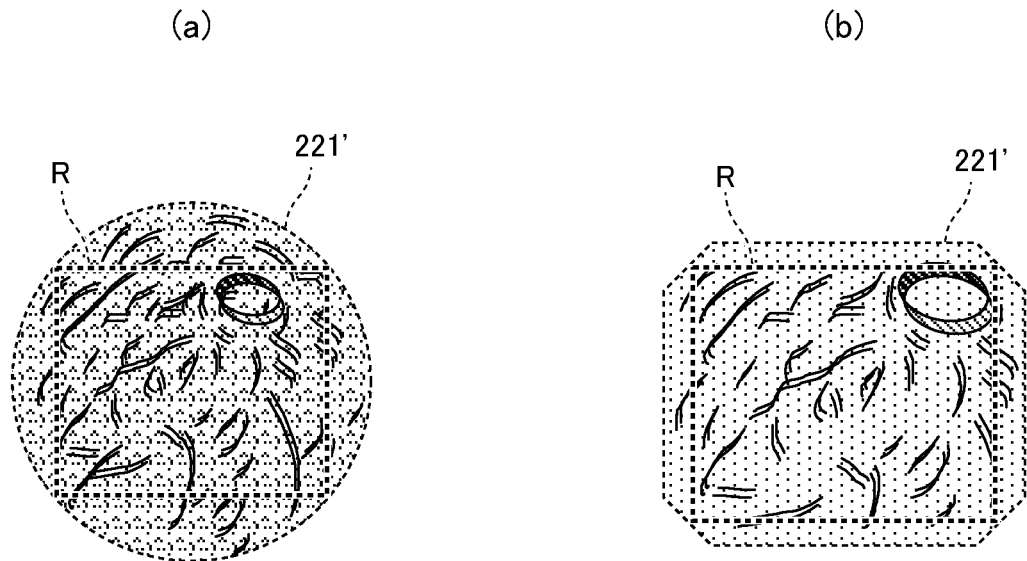
FIG. 7 is a diagram describing other examples of a process of establishing an image region in a region of change.

Additionally, there may be many variations regarding the method of determining the image region in the region of change 221'. FIG. 7 is a diagram describing other examples of a process of establishing the image region in the region of change 221'. FIG. 7(*a*) is a diagram showing a method of determining the rectangular region R where the region of change 221' is recognized by the establishing unit 113 to be a circle. The establishing unit 113 determines the rectangular region R that is inscribed in the circle of the region of change 221'. At this time, the rectangular region R is adjusted to match the aspect ratio that is set for the image region.

FIG. 7(*b*) is a diagram showing a method of determining the rectangular region R where the region of change 221' is recognized by the establishing unit 113 to be a polygon. The establishing unit 113 determines the rectangular region R that is inscribed in the polygon of the region of change 221'. Also at this time, the rectangular region R is adjusted to match the aspect ratio that is set for the image region. In either case, the candidate image region or the image region may be established by performing a coordinate averaging process on the rectangular region R that is determined in relation to each of a specified number of difference images that are successively generated, as described above.

Figure 8:
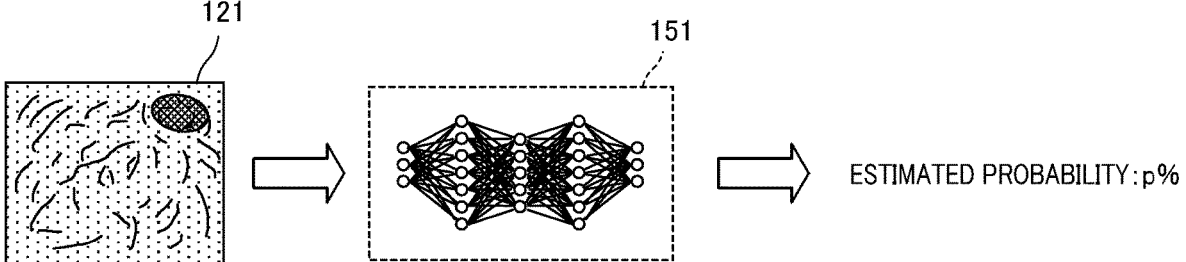
FIG. 8 is a diagram describing a procedure of an analysis process performed using a trained model.

Next, an analysis process by the diagnosis support unit 114 will be described. FIG. 8 is a diagram describing a procedure of an analysis process performed using the neural network for analysis 151 that is a trained model. The neural network for analysis 151 is created in advance by supervised learning where a large number of images including a lesion and a large number of images not including a lesion are provided together with respective ground truths. The neural network for analysis 151 created in this manner is stored in the storage unit 150, and is provided for use by being read by the diagnosis support unit 114 as appropriate.

As described above, the endoscope system 200 receives the captured image from the camera unit 210 that is inserted into the stomach of the subject at 60 fps, for example, and in a case where a release signal is generated by the doctor, a still image is received as the captured image. The display signal that is received by the examination support device 100 from the endoscope system 200 in this case is, as the display signal, a 60-fps frame signal, but the captured image 121 that is generated by being cut out therefrom is a pseudo still image that is frozen for a certain period of time.

As described with reference to FIG. 3, after detecting the captured image 121 to be the pseudo still image and generating the captured image data, the acquisition unit 111 transfers the captured image data to the diagnosis support unit 114 as diagnosis target image data. The diagnosis support unit 114 inputs the captured image 121 obtained by developing the captured image data that is received to the neural network for analysis 151, and causes the estimated probability to be calculated.

Figure 9:
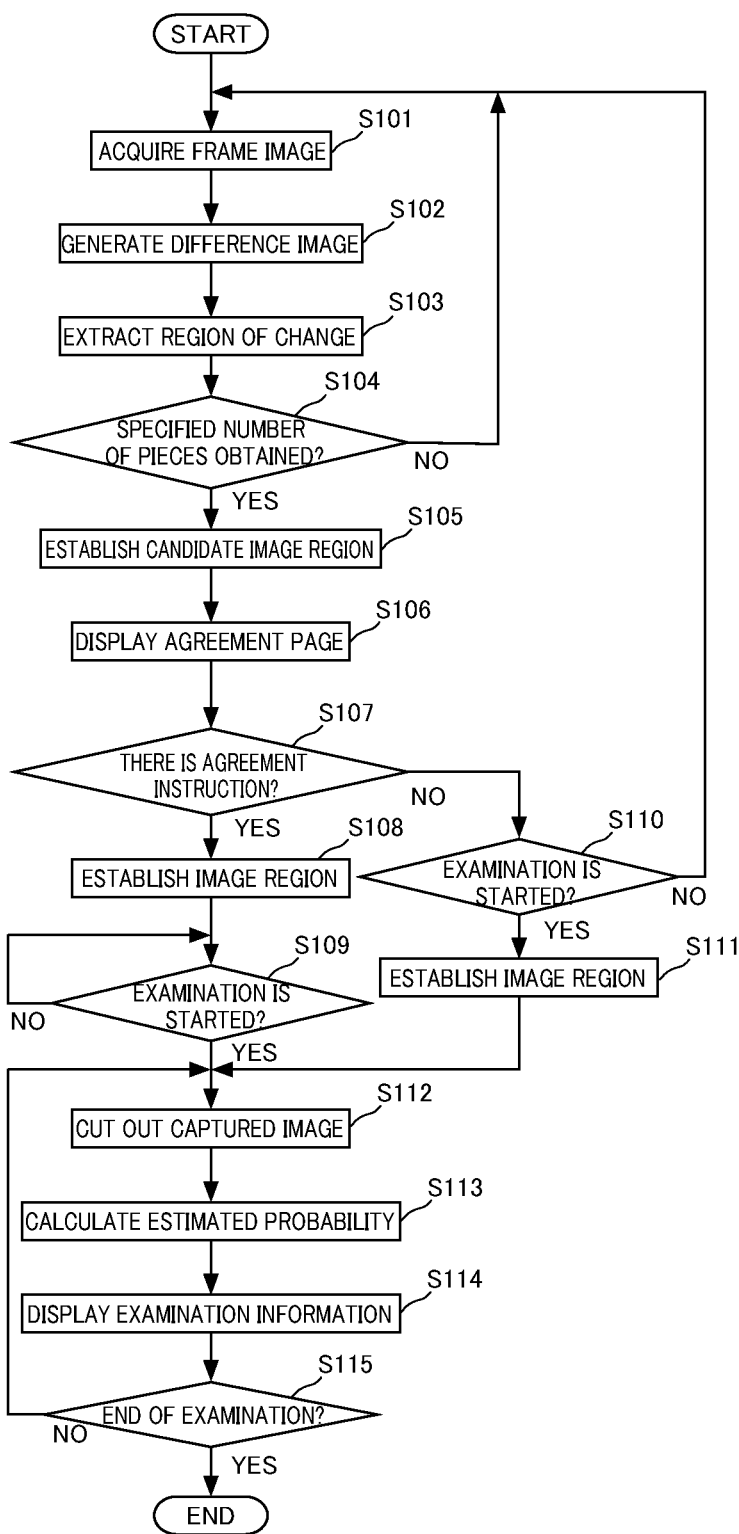
FIG. 9 is a flowchart describing a processing procedure of an arithmetic processing unit.

Next, a processing procedure of an examination support method performed using the examination support device 100 will be described. FIG. 9 is a flowchart describing a processing procedure that is performed by the arithmetic processing unit 110. For example, the flow is started when the endoscope system 200 and the examination support device 100 are activated.

In step S101, the acquisition unit 111 sequentially acquires the display signal that is transmitted from the endoscope system 200, develops the same into the regenerated signal image 225, and transfers the same to the detection unit 112 as the frame image. In step S102, the detection unit 112 generates the difference image 226 from successive frame images in the manner described with reference to FIG. 4, and transfers the same to the establishing unit 113. In step S103, the establishing unit 113 determines the region of change 221' in each frame image in the manner described with reference to FIG. 5, and determines the rectangular region R in the region of change 221'.

The establishing unit 113 proceeds to step S104, and determines whether coordinate information of a specified number of rectangular regions R has been obtained from the difference images that are successively generated. In the case where it is determined that the coordinate information has not been obtained, step S101 is performed again. In the case where it is determined that the coordinate information has been obtained, step S105 is performed next.

After proceeding to step S105, the establishing unit 113 establishes the candidate image region based on the coordinate information of the specified number of rectangular regions R obtained, and transfers coordinate information of the candidate image region to the display control unit 115. In step S106, the display control unit 115 displays the agreement page shown in FIG. 6 on the display monitor 120. In step S107, the establishing unit 113 checks whether an agreement instruction is received or not. In the case where reception is determined, step S108 is performed next. In the case where reception is not determined within a certain period of time, step S110 is performed next.

After proceeding to step S108, the establishing unit 113 establishes, based on the candidate image region with respect to which agreement is received, which region in the image region of the regenerated signal image 225 generated from the image signal is the image region indicating the captured image. When the image region is established, step S109 is performed next, and the arithmetic processing unit 110 is on standby until examination is started.

In the case where step S110 is performed following step S107, the arithmetic processing unit 110 determines whether the examination is started or not. In the case where it is determined that the examination is not started, step S101 is performed again to start over from establishment of a new candidate image region. Additionally, instead of establishing a new candidate image region, an image region may be established by making the doctor move the region outline indicator 126 by receiving a drag operation on the touch panel, for example.

In the case where it is determined in step S110 that the examination is started, step S111 is performed next, and the establishing unit 113 establishes the candidate image region established in step S105, as the image region indicating the captured image, without agreement of the doctor. In other words, the doctor may cause the candidate image region to be established as the image region without performing an agreement operation on the agreement page, simply by starting the examination. Additionally, for example, the arithmetic processing unit 110 determines that the examination is started at a time point when it is confirmed that an image shown in the candidate image region changed to an image of an inside of a mouth.

When the image region indicating the captured image is established, and the examination is started, the acquisition unit 111 cuts out, in step S112, the captured image 121 from the frame image that is developed from the display signal that is acquired, according to the image region that is established, and transfers the captured image 121 to the diagnosis support unit 114. In step S113, the diagnosis support unit 114 calculates the estimated probability as described above, and transfers the same to the display control unit 115. In step S114, the display control unit 115 displays the examination information on the display monitor 120 according to a display mode as shown in the bottom drawing in FIG. 3. The arithmetic processing unit 110 repeats step S112 to step S114 until an instruction to end the examination is received in step S115. When the instruction to end the examination is received, the series of processes is ended.

Figure 10:
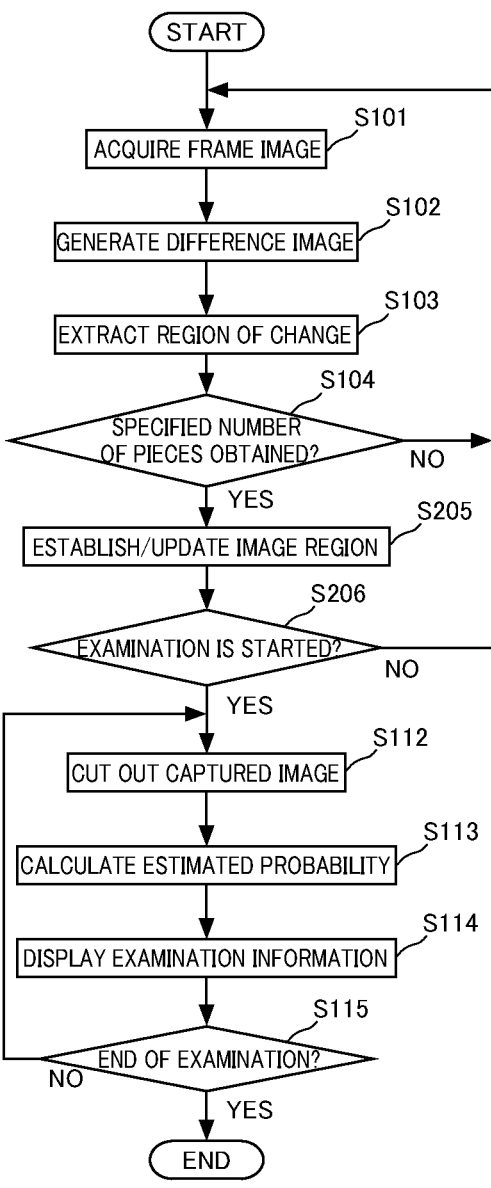
FIG. 10 is a flowchart describing another example of the processing procedure of the arithmetic processing unit.

FIG. 10 is a flowchart describing another example of the processing procedure that is performed by the arithmetic processing unit 110. The processing procedure shown in FIG. 10 is different from the processing procedure in FIG. 9 in that the agreement of the doctor is not required, and in that the image region that is established is updated until the examination is started. Processes that are approximately the same as those in FIG. 9 are denoted by same step numbers as the step numbers in FIG. 9, and description thereof is omitted.

In the case where it is determined in step S104 that the coordinate information of a specified number of rectangular regions R has been obtained from the difference images that are successively generated, the establishing unit 113 proceeds to step S205. In step S205, the establishing unit 113 establishes the image region based on the coordinate information of the specified number of rectangular regions R obtained. In step S206, the arithmetic processing unit 110 determines whether the examination is started or not. In the case where it is determined that the examination is not started, the process returns to step S101. When the process returns to step S101, step S101 to step S104 are performed again, and in the case where the process proceeds to step S205, the image region that is already established is updated to the image region that is newly calculated.

In the case where it is determined in step S206 that the examination is started, the arithmetic processing unit 110 proceeds to step S112. More specifically, for example, in the case where it is confirmed that the image indicated by the image region that is established changed to an image of an inside of a mouth, it is determined that the camera unit 210 is inserted into the mouth of the subject and that the examination is started, and update of the image region is stopped, and step S112 is performed. The following processes are the same as the processes in FIG. 9. Additionally, in the case where it is determined by an interrupt process that the examination is started, while the processes following step S101 are being performed after the image region is once established, it is possible to jump to step S112.

In the present embodiment described above, as described with reference to FIG. 4, each frame image is converted into gray scale, a difference in pixel values is calculated between corresponding pixels as the amount of difference, and the difference image 226 is thus generated, but the method of evaluating the amount of difference or the method of generating the difference image is not limited to the one described above. For example, pixels forming the difference image may be categorized into two types based on whether there is a difference in each of the pixels (the amount of difference is 1 or more) or not (the amount of difference is 0), and when the difference is determined to be present in a reference number of difference images (for example, two difference images) or more, among a predetermined number of successive difference images (for example, eight difference images), with respect to the corresponding pixel, the pixel may be evaluated to be a pixel included in the region of change. In this case, as a reference amount, a first reference amount used for categorization based on whether there is a difference or not, and a second reference amount for performing sorting in relation to the number of difference images where there is a difference, among the predetermined number of successive difference images, are set. Furthermore, for example, a per-pixel motion vector may be calculated between frame images, and a size of the motion vector may be taken as the amount of difference. In this case, the reference amount is also set in the form of a size of a reference vector that is adjusted to match an actual state.

Furthermore, in the present embodiment described above, a case is assumed where the endoscope system 200 and the examination support device 100 are connected by the connection cable 250, but wireless connection may also be adopted instead of wired connection. Furthermore, an embodiment is described where the endoscope system 200 outputs a display signal to outside, and where the examination support device 100 uses the display signal, but the format of an output signal is not particularly specified as long as an image signal that is provided to an external device by the endoscope system 200 includes the image signal of the captured image that is captured by the camera unit 210.

Furthermore, in the present embodiment described above, an example where the examination target is the stomach is described, but the endoscope system 200 does not have to be specialized for stomach examination, and may also be used for examination of other parts. For example, the examination support device 100 that is connected to the endoscope system 200 for examining a duodenum is a device that calculates and displays a probability of existence of a lesion in a captured image of the duodenum. In this case, the neural network for analysis 151 corresponding to a part that is the examination target is prepared in advance. Moreover, in the present embodiment described above, a description is given assuming that the camera unit 210 of the endoscope system 200 is a flexible endoscope, but the configuration and processing procedures of the examination support device 100 are no different even when the camera unit 210 is a rigid endoscope.

REFERENCE SIGNS LIST

100 examination support device
110 arithmetic processing unit
111 acquisition unit
112 detection unit
113 establishing unit
114 diagnosis support unit
115 display control unit
120 display monitor
121 captured image
122 diagnosis support information
122' support information
122a numerical value information
122b title text
122c graphics
125 regenerated signal image
126 region outline indicator
127 inquiry text
128 enter icon
130 input/output interface
140 input device
150 storage unit
151 neural network for analysis
200 endoscope system
210 camera unit
220 system monitor
221 captured image
221' region of change
222 examination information
222' region of no change
225 regenerated signal image
226 difference image
250 connection cable

The invention claimed is:

1. An examination support device that is used by being connected, via a wired or wireless connection, as one of external devices capable of receiving an image signal provided by an endoscope system including a camera unit for being inserted into an inside of a body of a subject, the examination support device comprising:

a processor coupled to a memory storing instructions for the processor to function as:

an acquisition unit for sequentially acquiring the image signal corresponding to a display image, which includes an image region representing a captured image taken by the camera unit and another region, the image signal being provided by the endoscope system to the one of the external devices capable of receiving the image signal;

a detection unit for detecting a difference between successive frame images in relation to frame images that are sequentially generated from the image signals;

an establishing unit for establishing the image region indicating a captured image that is captured by the camera unit, based on a region of change where an amount of difference of the difference detected by the detection unit is equal to or greater than a reference amount; and a diagnosis unit for performing diagnosis of the inside of the body by inputting, to a trained model, a diagnosis image that is generated by cutting out the image region established by the establishing unit from the frame image, wherein the establishing unit establishes the image region based on an aspect ratio that is required of an image to be input to the trained model.

2. The examination support device according to claim 1, wherein the establishing unit determines the image region as a rectangular shape that is inscribed in the region of change.

3. The examination support device according to claim 1, wherein the establishing unit superimposes an indicator on a display monitor that displays the frame image, to enable a candidate region as a candidate for the image region to be visually recognized, and establishes the candidate region as the image region in a case where an instruction indicating agreement is received from a user.

4. The examination support device according to claim 1, wherein the detection unit continues to detect the difference between the frame images also after the image region is established by the establishing unit, and the establishing unit updates the image region based on the region of change.

5. The examination support device according to claim 4, wherein the establishing unit stops updating the image region after insertion of the camera unit into a mouth of the subject is detected.

6. An examination support method performed using an examination support device that is used by being connected, via a wired or wireless connection, as one of external devices capable of receiving an image signal provided by an endoscope system including a camera unit for being inserted into an inside of a body of a subject, the examination support method comprising:

an acquisition step of sequentially acquiring the image signal corresponding to a display image, which includes an image region representing a captured image taken by the camera unit and another region, the image signal being provided by the endoscope system to the one of the external devices capable of receiving the image signal;

a detection step of detecting a difference between successive frame images in relation to frame images that are sequentially generated from the image signals;

an establishing step of establishing the image region indicating a captured image that is captured by the camera unit, based on a region of change where an amount of difference of the difference detected in the detection step is equal to or greater than a reference amount; and a diagnosis step of performing diagnosis of the inside of the body by inputting, to a trained model, a diagnosis image that is generated by cutting out the image region established by the establishing unit from the frame image, wherein the establishing step establishes the image region based on an aspect ratio that is required of an image to be input to the trained model.

7. A non-transitory computer-readable storage medium storing an examination support program for controlling an examination support device that is used by being connected, via a wired or wireless connection, as one of external devices capable of receiving an image signal provided by an endoscope system including a camera unit for being inserted into an inside of a body of a subject, the examination support program being for causing a computer to perform:

an acquisition step of sequentially acquiring the image signal corresponding to a display image, which includes an image region representing a captured image taken by the camera unit and another region, the image signal being provided by the endoscope system to the one of the external devices capable of receiving the image signal;

a detection step of detecting a difference between successive frame images in relation to frame images that are sequentially generated from the image signals; and an establishing step of establishing the image region indicating a captured image that is captured by the camera unit, based on a region of change where an amount of difference of the difference detected in the detection step is equal to or greater than a reference amount; and a diagnosis step of performing diagnosis of the inside of the body by inputting, to a trained model, a diagnosis image that is generated by cutting out the image region established by the establishing unit from the frame image, wherein the establishing step establishes the image region based on an aspect ratio that is required of an image to be input to the trained model.

* * * * *